United States Patent [19]

Iinuma et al.

[11] 4,253,338
[45] Mar. 3, 1981

[54] ULTRASONIC DIAGNOSTIC EQUIPMENT

[75] Inventors: Kazuhiro Iinuma, Yokohama; Takeshi Kidokoro, Hiratsuka; Kinya Takamizawa, Yokohama, all of Japan

[73] Assignee: Tokyo Shibaura Electric Co., Ltd., Kawasaki, Japan

[21] Appl. No.: 791,401

[22] Filed: Apr. 27, 1977

[30] Foreign Application Priority Data

Apr. 28, 1976 [JP] Japan .................................. 51/49299

[51] Int. Cl.³ ............................................ G01N 29/00
[52] U.S. Cl. ..................................... 73/626; 128/660; 367/105
[58] Field of Search.. 128/2.05 Z, 2 V, 660–663 (U.S. Only); 73/607, 610 (U.S. Only), 628, 67.85, 71.5 US, 618–621, 624–626; 340/5 MP, 9, 1 R; 367/105

[56] References Cited

U.S. PATENT DOCUMENTS

| 3,693,415 | 9/1972 | Whittington | 73/619 X |
|---|---|---|---|
| 3,713,329 | 1/1973 | Munger | 128/2 V X |
| 3,778,756 | 12/1973 | Houston et al. | 128/2.05 Z X |
| 3,805,596 | 4/1974 | Klahr | 128/2.05 Z X |
| 3,881,466 | 5/1975 | Wilcox | 128/2 V |
| 3,888,238 | 9/1973 | Meindl et al. | 128/2.05 Z |
| 3,919,683 | 11/1975 | Itamura et al. | 73/626 |
| 3,939,696 | 2/1976 | Kossoff | 73/626 |
| 4,005,382 | 1/1977 | Beaver | 340/6 R X |
| 4,016,862 | 4/1977 | Lancee et al. | 128/2 V |
| 4,019,169 | 9/1975 | Takamizawa | 73/626 |
| 4,075,598 | 2/1978 | Takamizawa et al. | 73/626 |
| 4,136,325 | 1/1979 | Takamizawa et al. | 73/626 |

OTHER PUBLICATIONS

Lancaster, D. L. "TTL Cookbook", Howard Sams & Co., 1974, pp. 144–149.

Primary Examiner—Robert W. Michell
Assistant Examiner—Francis J. Jaworski
Attorney, Agent, or Firm—Oblon, Fisher, Spivak, McClelland & Maier

[57] ABSTRACT

An ultrasonic diagnostic equipment of linear electric scanning type includes a plurality of pulse generators for supplying electric pulses to a plurality of ultrasonic transducers disposed on a plane, gate circuits for driving the pulse generator, a plurality of analogue switching circuits for selecting the reflected ultrasonic pulse signals received by the ultrasonic transducers, and a control circuit for controlling these pulse generators and switching circuits. The control circuit synchronizingly controls the operations of the gate circuits and analogue switching circuits in order to operate a given number of ultrasonic transducers of the plural of the ultrasonic transducers. The pulse generator and switching circuit are provided corresponding to each transducer.

6 Claims, 6 Drawing Figures

ULTRASONIC DIAGNOSTIC EQUIPMENT

BACKGROUND OF THE INVENTION

The present invention relates to an ultrasonic diagnostic equipment and, more particularly, to the one of linear electronic scanning type for electronically moving in parallel the ultrasonic beam.

An ultrasonic scanning type diagnostic equipment has a plurality of ultrasonic transducers. Any selected one of the transducers emits an ultrasonic beam to a living body. The equipment receives pulses reflected from the living body and displays an image of the living body based on the reflected pulses. Such an equipment is disclosed in U.S. Pat. Nos. 3,789,833 and 3,881,466. The specifications of these U.S. patents, however, do not describe in detail a scanning circuit for driving and switching the ultrasonic transducers of the equipment. In the conventional linear electronic scanning type diagnostic equipment, the ultransonic transducers are switched on and off one after another. To drive any one of the transducers a switching circuit is employed to control not only the voltage of the pulses reflected from a living body but also the voltage of the input pulses to the transducer.

Generally, input pulses to drive an utlrasonic transducer have a relatively high voltage, e.g. tens to hundreds of volts. A switching circuit applied with such a high voltage will inevitably generate pulses each time it is operated. The unnecessary ultrasonic pulses thus produced will result in a virtual or ghost image of the living body. Of course, the switching circuit is made to withstand a high voltage and a great current. As a result, it cannot detect input signals at the best possible signal/noise (S/N) ratio. Such a switching circuit is indispensable to the conventional ultrasonic scanning type diagnostic equipment. This is why the equipment has a complicated circuit construction and is very costly.

SUMMARY OF THE INVENTION

An object of the present invention is to provide an ultrasonic diagnostic equipment of which the circuit construction is simple and economical.

Another object of the present invention is to provide an ultrasonic diagnostic equipment in which any virtual image by the switching operation and the coupling among signals corresponding ultrasonic transducers does not appear and the S/N ratio is improved.

Yet another object of the present invention is to provide an ultrasonic diagnostic equipment capable of effecting the phase control such as electronic focusing in an easy manner.

In one form of the preferred embodiments of the present invention, there is provided an ultrasonic diagnostic equipment having a plurality of ultrasonic transducers disposed on a plane, a scanning circuit for successively scanning a predetermined number of transducers of these ones, and a device for processing the signal received by the ultrasonic transducers, in which the scanning circuit comprises: pulse generators connected correspondingly to the transducers for generating ultrasonic pulses; first switching means connected to the pulse generators for selectively driving the pulse generators; second switching means connected to the transducers for selectively receiving a receiving signal; and a control circuit for selectively driving the first and second switching means.

Other objects and features of the present invention will be apparent from the following description taken in connection with the accompanying drawings, in which.

DESCRIPTION OF THE PREFERRED EMBODIMENTS

Figure 1:
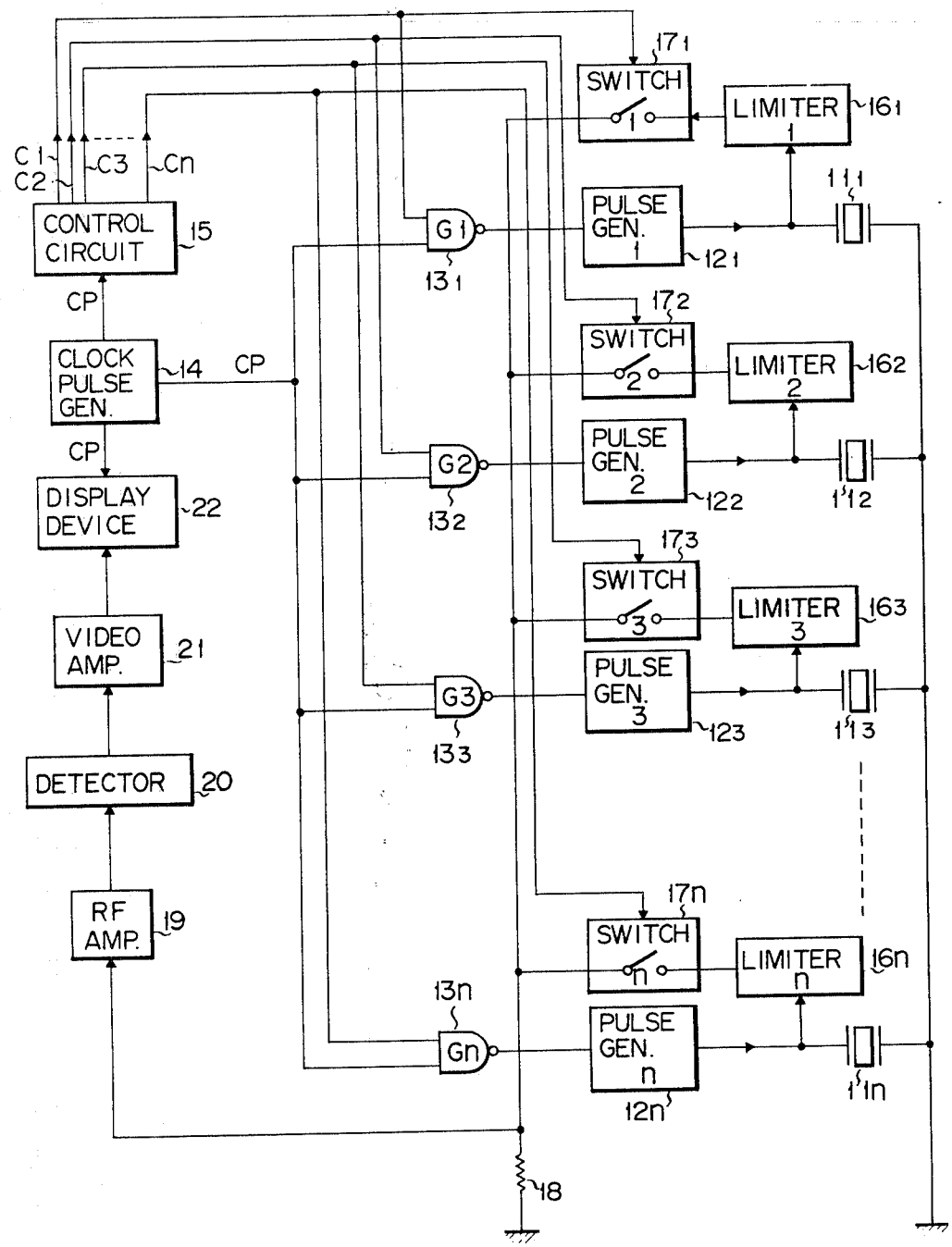
FIG. 1 is a block diagram of an ultrasonic diagnostic equipment of a linear electronic scanning type.
Figure 2:
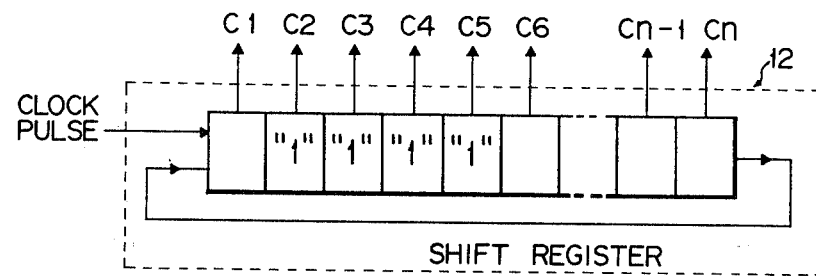
FIG. 2 is a circuit diagram of a control circuit of the FIG. 1 equipment.
Figure 3:
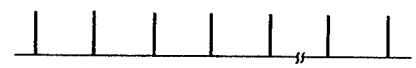
FIG. 3 is a set of timing diagrams for illustrating the relation of the control circuit and a clock pulse generator in FIG. 1.
Figure 3:
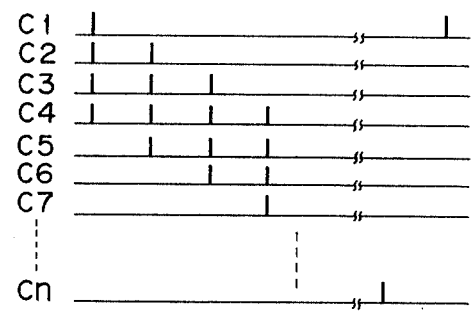

Referring now to FIG. 1, there is shown a principle circuit of an ultrasonic diagnostic equipment of a linear scanning type according to the present invention. Reference numerals $11_1$ to $11_n$ designate ultrasonic transducers each piezoelectric elements for effecting electric to acoustic or acoustic to electric conversion. These transducers $11_1$ to $11_n$ are arranged in collective fashion so as to be disposed at equal intervals on a plane or a circular surface of a human body. When these transducers $11_1$ to $11_n$ are applied to a living body, one of the electrodes of each transducers is grounded for ensuring a safety of the living body. The grounding prevents damage of the living body due to surge current or large current. Pulse generators $12_1$ to $12_n$ are provided corresponding to the ultrasonic transducers $11_1$ to $11_n$ and produce pulses to be supplied to the corresponding ultrasonic transducers, respectively. These pulses are generated by a clock pulse generator to be described later and are short pulses having a several MHz frequency bandwidth and several tens to several hundreds of volts. A digital gate circuit for selectively driving pulse generators $12_1$ to $12_n$ may be constructed of, for example, NAND gates $13_{/1}$ and $13_n$. These NAND gates provided for the pulse generators $12_1$ to $12_n$ are of TTL operable at a low voltage. The digital gate may be constructed of AND gate. The clock pulse generator 14 generates clock pulses CP of 1 to 4 KHz, for example. Upon receipt of the clock pulses CP, a control circuit 15 generates given control signals C1 to Cn. As shown in FIG. 2, the control circuit 15 is serial-parallel shift register with given bit length of 64 bits, for example. The control circuit 15 shifts stored information comprising a series of bits (for example, 4 bits) having each logical level "1", when receiving each clock pulse CP. The most significant bit and the least significant bit are connected to each other to permit a series of continuous information to circulate therein. Therefore, the control circuit 15 outputs control signals $C_1$ to $C_n$ by shifting one bit, as shown in FIG. 3, when receiving the clock pulse CP. The number of control signals $C_1$ to $C_n$ is the same as that of the ultrasonic transducers $11_1$ to $11_n$.

Control signals $C_1$ to $C_n$ from the control circuit 15 are coupled to one side input terminals of the corresponding NAND gates $13_1$ and $13_n$, while clock pulses CP are coupled commonly to the other side input terminals of the same.

Converted electrical signals, e.g. reflection pulses reflected in the living body, appear at the outputs of the transducers $11_1$ to $11_n$. The reflection pulses have small amplitude as compared with the drive pulses for wave transmission from the pulse generator. The transducers $11_1$ to $11_n$ are connected at the outputs to corresponding limiters $16_1$ to $16_n$, respectively, which restrict the amplitude of the drive pulses for wave transmission to a value predetermined thereby to permit only the reflection pulses to pass. These limiters $16_1$ to $16_n$ are connected correspondingly to switching circuits $17_1$ to $17_n$, respectively, but can be omitted if the pulses from the pulse generators are not too high to be accepted by analog switches. These switching circuits $17_1$ to $17_n$ are analog switches which are turned on when the control signals $C_1$ to $C_n$ from the control circuit 15 are applied thereto. These switching circuits are controlled by the control circuit 15 in the above-mentioned manner. The switching circuit is comprised of an analog switch made of junction FET's or switching diodes. The switching circuit may also be constructed of the commercially available FET analog switch DG140 (Siliconics Company Ltd.). The output terminals of the respective switching circuits $17_1$ to $17_n$ are connected with signal addition means. The signal addition means equivalently is expressed in terms of a resistor 18 commonly connected between the output terminals of the switching circuit $17_1$ and $17_n$ and the ground, and serves to add the signals appearing at the output terminals of the switching circuits $17_1$ to $17_n$.

The signal addition means 18 is connected to a signal processing means which process the signals for visualizing the output signals from the signal addition means 18. The signal processing means comprises a high frequency amplifying circuit 19 for amplifying the output signal from the signal addition means 18, a detector 20 for detecting the output from the output of the amplifying circuit 19, a video amplifier 21 for amplifying the output of the detector 20, and a display device 22 for visualizing the output signal from the video amplifier. The display device 22 receives the clock pulses CP from the clock pulse generator 14 and, in operation, synchronizes with the generation of ultrasonic pulses and the switching of the reflection pulses. The signal processing means may be constructed by using conventional display techniques.

Figure 4:
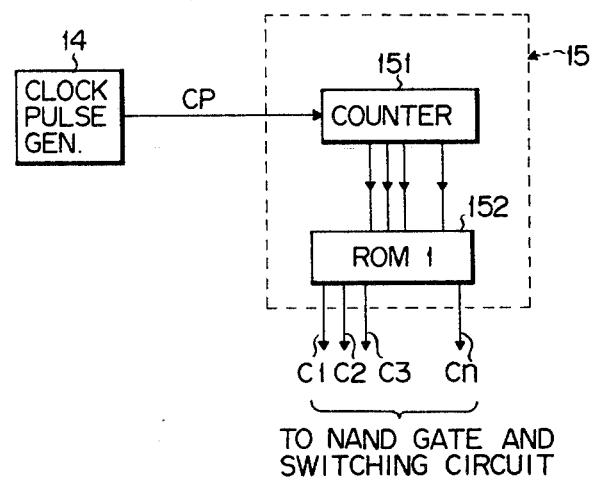
FIG. 4 is a block diagram of a modification of the control circuit of FIG. 1.

The control circuit 15 mentioned above may be constructed as shown in FIG. 4. That is, the circuit comprises a counter 151 for successively counting the clock pulse CP from the clock pulse generator 14 and a read only memory (ROM) 152 in which the given control information $C_1$ to $C_n$ corresponding to the transducers are stored and these information are read out by addressing of the contents of the counter 151. If the number of the transducers is 64, the counter 151 is a 64 scale counter. The counts of the counter 151 and the addresses and the output of the ROM1 (152) are related as tabulated in Table 1. The counter 151 counts the clock pulse CP from the clock pulse generator 14. The output of the counter 151 addresses the ROM1 (152) to read out desired control signals $C_1$ to $C_n$. The control signals are applied to the NAND gates and the switching circuits to operate given transducers. In this case, four transducers are simultaneously driven and shifted one by one in response to one clock pulse.

TABLE 1

| COUNTER OUTPUT | ROM1 ADDRESS | ROM1 OUTPUT C1, C2, C3, C4 ... Cn |
|---|---|---|
| 1 | 1 | 1 1 1 1 0 0 . . . . . 0 |
| 2 | 2 | 0 1 1 1 1 0 . . . . . 0 |
| 3 | 3 | 0 0 1 1 1 1 . . . . . 0 |
| . | . | . |
| . | . | . |
| 61 | 61 | 0 0 0 0 0 0 . . . 1 1 1 1 |
| 62 | 62 | 1 0 0 0 0 0 . . . 0 1 1 1 |
| 63 | 63 | 1 1 0 0 0 0 . . . 0 0 1 1 |
| 64 | 64 | 1 1 1 0 0 0 . . . 0 0 0 1 |
| 1 | 1 | 1 1 1 1 0 0 . . . 0 |
| . | . | . |
| . | . | . |

In actual use for measuring the living body, the ultrasonic diagnostic equipment is operated and the collective body of the ultrasonic transducers $11_1$ to $11_n$ is made to closely contact the living body. The clock pulse generator 14 generates clock pulses CP which are in turn fed to the control circuit 15. In response to the clock pulses CP, the control circuit 15 generates simultaneously four series of control signals, as shown in FIG. 3. Every application of the clock pulse CP, the four series of clock pulses are successively shifted one by one.

Assume now that the control signals $C_2$ to $C_5$ are produced from the control circuit, as shown in FIG. 2. The control signals $C_2$ to $C_5$ are applied to the corresponding NAND gates $13_2$ to $13_5$, respectively. With application of the clock pulses CP to the NAND gates $13_2$ to $13_5$, the NAND gates $13_2$ to $13_5$ produce signals with logical level "1" at the outputs. The output signals of "1" level are applied to the corresponding transducers $11_2$ to $11_5$ for driving them. Electrical signals of the pulse generators $12_2$ to $12_5$ are applied to the transducers $11_2$ to $11_5$ where they are converted into ultrasonic pulses. The ultrasonic pulses are radiated into the living body and they are reflected on the internal organs of the living body. The reflected pulses are then converted into electrical signals in the transducers $11_2$ to $11_5$ which in turn are applied to the switching circuits $17_2$ to $17_5$ through the limiters $16_2$ to $16_5$. At this time, since control signals $C_2$ to $C_5$, the same as those applied to the NAND gates $13_2$ to $13_5$, are fed to the switching circuits $17_2$ to $17_5$, the switching circuits are in ON condition. Therefore, ultrasonic pulses received by the transducers $11_2$ to $11_5$ are applied to the signal addition means 18 through the corresponding limiters $16_2$ to $16_5$ and the switching circuits $17_2$ to $17_5$. The reflection pulses voltage-added in the signal addition means 18 are fed to the display device 22 through the high frequency amplifier 19, the detector 20 and the video amplifier 21.

When the succeeding clock pulse CP is applied to the control circuit 15, four series of control signals $C_3$ to $C_6$ shifted by one are simultaneously produced from the control circuit 15. In this case, as in the previous case, the transducers $11_3$ to $11_6$ corresponding to four control signals $C_3$ to $C_6$ are driven and the signals from the transducers $11_3$ to $11_6$ are visualized in the display device. That is, each clock pulse CP, four transducers successively shifted one by one. Otherwise, i.e. unless four transducers are simultaneously driven, the directivity of the ultrasonic beam radiated into the living body is deteriorated. In other words, if a narrow signal ultrasonic transducer is used to radiate ultrasonic beam into the living body, the ultrasonic beam spreads laterally, resulting in deterioration of the directivity. According to the method of the present invention, the image produced in the display device is clear and realistic.

In the ultrasonic diagnostic equipment of the invention, the pulse generators $12_1$ to $12_n$ are provided for the ultrasonic transducers $11_1$ to $11_n$, respectively, and the drive signal is selectively applied to these pulse generators by the output of the digital gate to drive a desired transducer. Therefore, there is no need of high voltage analog switching circuits of ultrasonic pulse transmission and a high voltage control circuit for controlling the switching circuits. Accordingly, the switching circuits $17_1$ to $17_n$ for selecting the ultrasonic receiving pulses received by the transducers may be constructed with low voltage switching circuit. Further, the pulse voltage produced when the switching circuits $17_1$ to $17_n$ are switched is extremely low because the switching circuit may be arranged with the low voltage switching element. For this, the receiving signal is little affected by the voltage pulses at the switching operation so that there is not produced virtual or ghost images in the display device thereby good images are obtained.

Further, the control circuit 15 may be constructed of the TTL circuit operable at low voltage which is commonly used with the pulse drive circuits $13_1$ to $13_n$ and, hence, the circuit construction is very simple. Since the analog switching elements used for the switching circuits $17_1$ to $17_n$ may be of low voltage and small current, low noise switching elements can selectively be used and the S/N ratio is improved resulting in cost reduction of the diagnostic equipment. In this case, the large output currents of the respective pulse generators $12_1$ to $12_n$ do not flow through a switching circuit or a long lead wire in the electronic circuit and are independent from the transducers $11_1$ to $11_n$. Accordingly, the isolation among the transducers $11_1$ to $11_n$ and corresponding circuits are good. The good isolation must be assured especially for the phase control such as electronic focusing.

It is to be noted here that, in the above-mentioned circuit, the pulse generator and switching circuits operating in synchronism with each other may be connected with separate transducers, respectively. The numbers of the pulse generator and the switching circuits, both being driven simultaneously, are not necessary equal. Further, the switching of the switching circuits may be performed at suitable intervals and not at each clock pulse.

Figure 5:
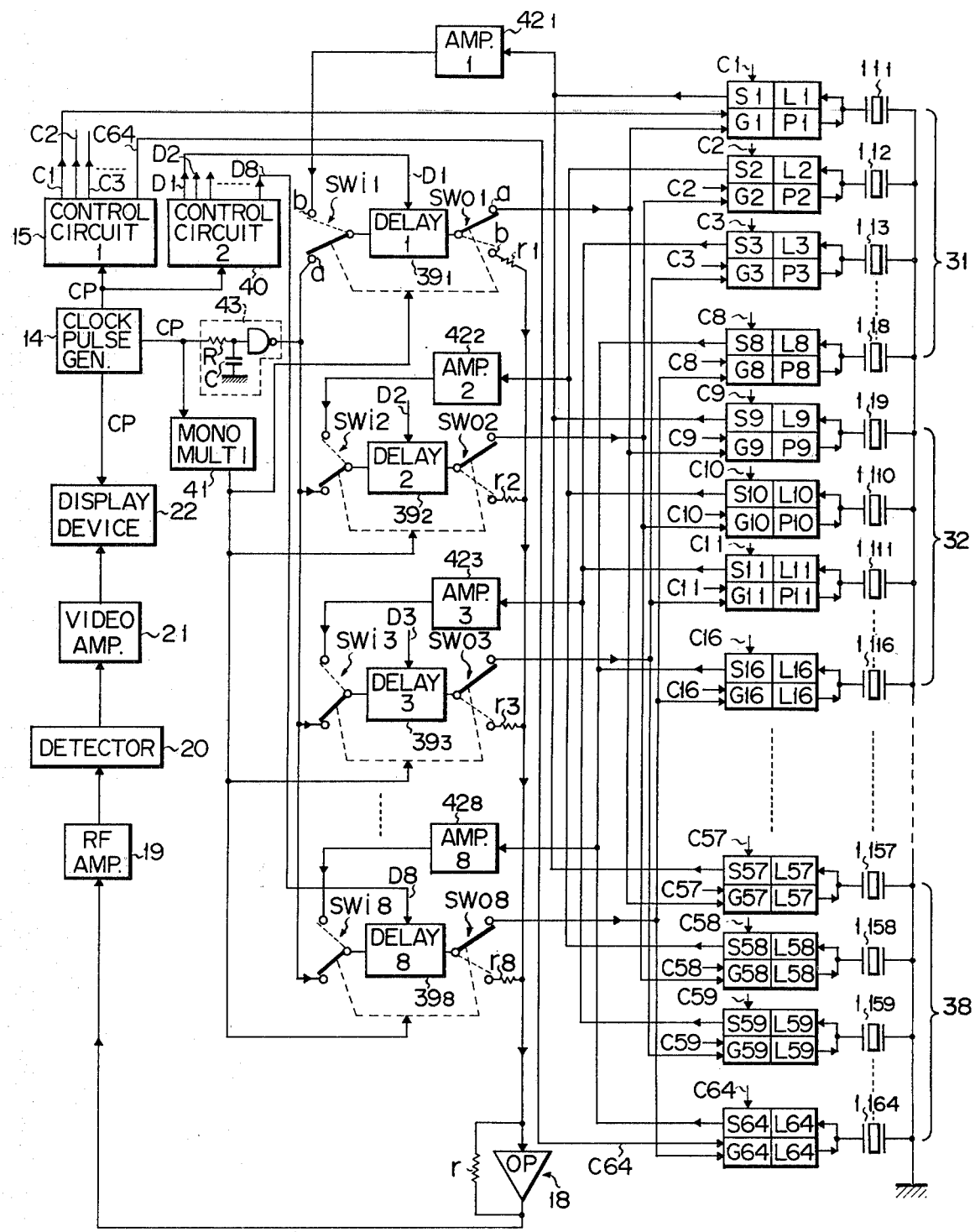
FIG. 5 shows a block diagram of another embodiment of an ultrasonic diagnostic equipment of the invention.

FIG. 5 shows another embodiment of the ultrasonic diagnostic equipment according to the present invention. The feature of the FIG. 5 embodiment resides in that the circuit with a phase controlling function is added to the FIG. 1 circuit. Further, the number of the ultrasonic transducers is 64 (n=64). In the figure, a letter S is used for switching circuits, G for NAND gates, P for the pulse generator, and L for limiters. Like reference numerals are used to designate like portions in FIG. 1. The ultrasonic transducers $11_1$ to $11_{64}$ are divided into groups 31, 32, ... 38, each group consisting of 8 transducers. The first group 31 corresponds to the ultrasonic transducers $11_1$ to $11_8$, the second group 32 to the transducers $11_9$ to $11_{16}$, and the eighth group 38 to the transducers $11_{57}$ to $11_{64}$. The corresponding transducers of the respective groups are commonly connected by variable delay lines $39_1$ to $39_8$. That is, the first position transducers of each group $11_1, 11_9, \ldots 11_{57}$ are connected by the variable delay line $39_1$, the second position transducers of each group $11_2, 11_{10}, \ldots 11_{58}$ are connected by the delay line $39_2$, and the last position transducers $11_8, 11_{16}, \ldots 11_{64}$ likewise are connected commonly by the delay line $39_8$. The delay times of these delay lines $39_1$ to $39_8$ are changed by delay control signals $D_1$ to $D_8$ to be described later. The variable delay lines $39_1$ to $39_8$ are each constructed of an LC delay line with 20 taps providing 200 nano second total delay of time. These delay lines $39_1$ to $39_8$ delay drive timings of the respective pulse generators $P_1$ to $P_{64}$ for supplying electrical signal pulses to the corresponding transducers $11_1$ to $11_{64}$, i.e. the timings of clock pulses CP to be supplied to the respective pulse generators $P_1$ to $P_{64}$, and analog electric signals of ultrasonic pulses received by the corresponding transducers $11_1$ to $11_{64}$. A switch (not shown) is used for selecting desired taps of the delay lines $39_1$ to $39_8$, and the desired time delay is selected by the delay control signal to be described later which is applied to the control terminal of the switch.

Upon receipt of clock pulses CP from the clock pulse generator 14, a delay control circuit 40 generates delay control signals $D_1$ to $D_8$ for controlling the delay time of the respective variable delay lines $39_1$ to $39_8$. The circuit 40 may also be constructed of the shift register, as in the previous case.

These variable delay lines $39_1$ to $39_8$ are connected at the input sides to switches $SWi1$ to $SWi8$ and at the output sides to the corresponding switches $SWo1$ to $SWo8$. These switches Swi and Swo are used for switching the input sides of the variable delay lines $39_1$ to $39_8$ in order to use these delay lines. These switches may be constructed of commercially available FET analog switches DG140 (Siliconics Company Ltd.). These switches SWi to SWo are interlocked to each other in operation. These switches are turned to a side at the leading edge of the output pulse of the monostable multivibrator 41 and to b side at the trailing edge thereof. In this case, the delay circuit 43 is provided after the clock pulse generator 14 in order that, after the a side of the switch is turned on, the clock pulse passes from the clock pulse generator 14. The delay circuit 43 is comprised of a resistor R and a capacitor C and a NAND circuit. The monostable multivibrator 41 is driven by the clock pulse from the clock pulse generator. Amplifiers $42_1$ to $42_8$ receive the reflection ultrasonic wave received by the respective transducers $11_1$ to $11_{64}$, through the limiter L and the switching circuit S and amplify it. The outputs of the amplifiers $42_1$ to $42_8$ are coupled to the b sides of the switches $SWi1$ to $SWi8$. The b contact sides of switches $SWo1$ to $SWo8$ are coupled to the signal addition means 18 through the resistor r1 to r8. In this case, the signal addition means 18 includes resistors r1 to r8 and an operational amplifier. In the signal addition means 18, accurate result of addition is obtained without any interference among the respective channels. The description will be omitted of the control circuit 15, the signal processing means (the high frequency amplifier 19, the detector 20, the video amplifier 21, the display device 22) for processing the signal from the signal addition means 18, the drive gate circuits $G_1$ to $G_{64}$, the pulse generators $P_1$ to $P_{64}$, the limiters $L_1$ to $L_{64}$, and the switching circuits $S_1$ to $S_{64}$, since the constructions and operations thereof are similar to those of FIG. 1.

(a) The operation will be described when the electronic focusing is made by the ultrasonic diagnostic equipment shown in FIG. 5. At this time, in the control circuit 15, continuous 8 bits are "1" level and shift one by one when receiving the clock pulse CP. Accordingly, the operation is executed each group 31, 32, . . . 38. When the clock pulse generator 14 produces the first clock pulse CP, the clock pulse CP is applied to the control circuit 15, the delay control circuit 40 and the monostable multivibrator 41. Accordingly, control signals C1 to C8 are generated from the control circuit 15, delay control signals $D_1$ to $D_8$ from the delay control circuit 40, and set output pulses from the monostable multivibrator 41. Switches SWi and SWo are turned to the a sides at the leading edge of the output pulse from the monostable multivibrator 41. Accordingly, the clock pulse CP is applied to the corresponding NAND gates $G_1$ to $G_8$, through the delay circuit 43, the switches SWi1 to SWi8, the variable delay lines $39_1$ to $39_8$, and the switches SWo1 to SWo8. On the other hand, since control signals $C_1$ to $C_8$ are applied to NAND gates $G_1$ to $G_8$, the outputs of NAND gates drive the corresponding pulse generators $P_1$ to $P_8$. As a result, the ultrasonic pulses from the corresponding transducers $11_1$ to $11_8$ are applied to the living body. In this case, the time delays $t_1$ to $t_8$ of the respective delay lines $39_1$ to $39_8$ are related as follows:

$$t_1=t_8,\ t_2=t_7,\ t_3=t_6,\ t_4=t_5\ \text{and}\ t_1<t_2<t_3<t_4$$

If the respective delay times are controlled to have the just-mentioned relations, the beam of the ultrasonic wave may be concentrated onto a desired position. Only the ultrasonic pulses received by the transducers $11_1$ to $11_8$ are applied to the amplifiers $42_1$ to $42_8$, through the switching circuits $S_1$ to $S_8$ and the limiters $L_1$ to $L_8$ which are selectively turned on by the control signals $C_1$ to $C_8$ delivered from the control circuit 15. The switches SWi and SWo are turned from the a side to the b side at the trailing edge of the output pulse from the monostable multivibrator 41, as indicated by a broken line. The outputs of the amplifiers $42_1$ to $42_8$ are added in the signal addition circuit 18 to which they are fed through the input side switches SWi1 to SWi8, the variable delay lines $39_1$ to $39_8$ and the output side switches SWo1 to SWo8. The output of the signal adder circuit in which the ultrasonic pulses reflected on a desired position of the living body are intensified is fed to the high frequency amplifier 19 and passes the detector 20 and the video amplifier 21 and finally is imaged on the screen of the display device.

(b) When the clock pulse generating circuit 14 generates the second clock pulse, the control signals $C_2$ to $C_9$ each shifted by one are outputted in response to the clock pulse CP. This means that the transducers $11_2$ to $11_9$ are selected. In this cycle of the second clock pulse, the NAND gates $G_2$ to $G_9$, the pulse generators $P_2$ to $P_9$, the limiters $L_2$ to $L_9$ and the switching circuits $S_2$ to $S_9$ are in operating condition. In this case, the delay times $t_1$ to $t_8$ of the variable delay lines $39_1$ to $39_8$ are related as follows:

$$t_2=t_1,\ t_3=t_8,\ t_4=t_7,\ t_5=t_6\ \text{and}\ t_2<t_3<t_4<t_5$$

The drive of the pulse generators $P_2$ to $P_9$, the generation of the ultrasonic pulses from the transducers $11_2$ to $11_9$, and the visualizing the reflection pulses from the living body, are much the same as of the above-mentioned article (a).

Through the repetition of similar operations each clock pulse, the phases of the ultrasonic pulses are electronically controlled so that both the electronic focusing and the linear electronic scanning are simultaneously attained.

Although the operation heretofore described relates to the electronic focusing, the ultrasonic diagnostic equipment according to the present invention may be applied to the compound scanning which is composed of the linear and the fan shaped scanning, or other phase controls, if the delay times of the delay lines $39_1$ to $39_8$ are properly controlled.

Figure 6:
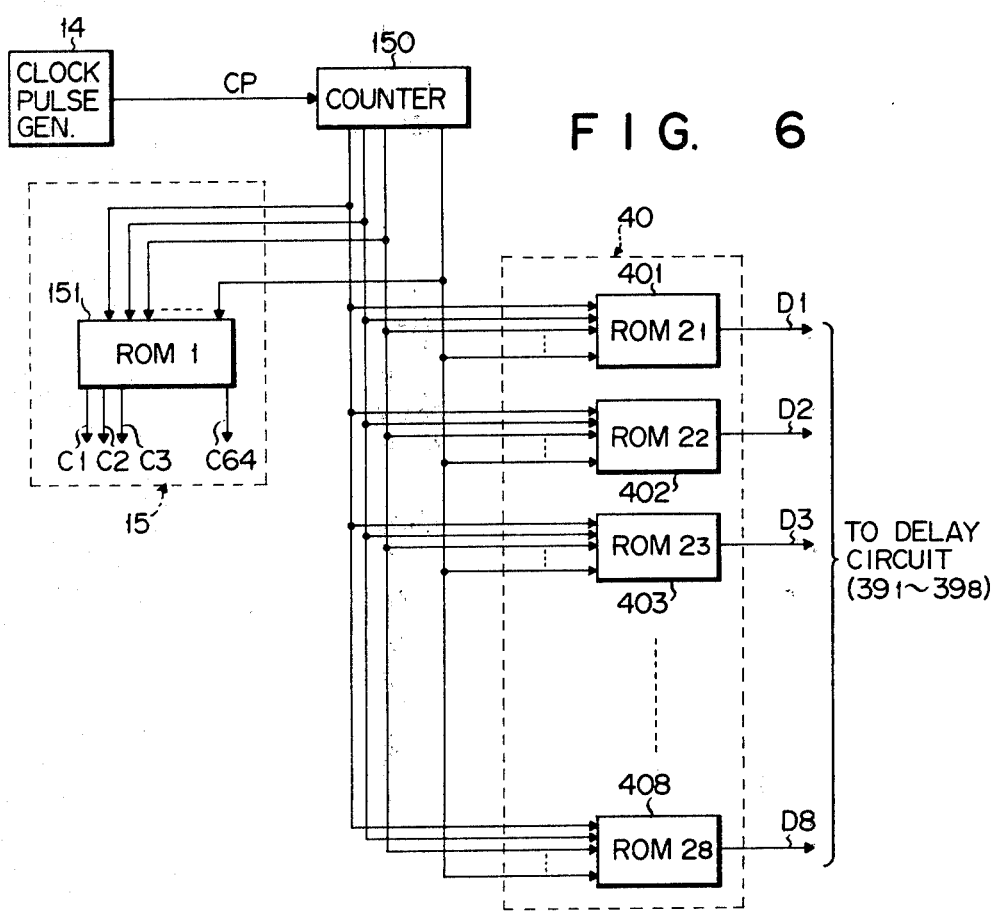
FIG. 6 is a block diagram of a modification of the FIG. 5 circuit.

The control circuit 1 (15) and the delay control circuit 2 (40) shown in FIG. 5 may be constructed as shown in FIG. 6. The control circuit 15 is constructed of the same ROM152 as the FIG. 4 ROM1 (152) in construction. The control circuit 40 is constructed of ROM2$_1$ (401) to ROM2$_8$ (408) provided corresponding to the delay lines $39_1$ to $39_8$. A counter 150 is used commonly for these memories ROM1 and ROM2 for addressing them. The addresses of the memories ROM2$_1$ to ROM2$_8$ and the related time control information are related as shown in Table 2.

TABLE 2

| COUNTER OUTPUT | ROM2$_1$-ROM2$_8$ ADDRESS | ROM2$_1$ OUTPUT | ROM2$_2$ OUTPUT | ROM2$_3$ OUTPUT | ... | ROM2$_8$ OUTPUT |
|---|---|---|---|---|---|---|
| 1 | 1 | $t_1$ | $t_2$ | $t_3$ | | $t_1$ |
| 2 | 2 | $t_1$ | $t_1$ | $t_2$ | | $t_2$ |
| 3 | 3 | $t_2$ | $t_1$ | $t_1$ | | $t_3$ |
| 4 | 4 | $t_3$ | $t_2$ | $t_1$ | | $t_4$ |
| 5 | 5 | $t_4$ | $t_5$ | $t_2$ | | $t_4$ |
| 6 | 6 | $t_4$ | $t_4$ | $t_3$ | | $t_3$ |
| 7 | 7 | $t_3$ | $t_4$ | $t_4$ | | $t_2$ |
| 8 | 8 | $t_2$ | $t_3$ | $t_4$ | | $t_1$ |
| 9 | 9 | $t_1$ | $t_2$ | $t_3$ | | $t_1$ |
| 10 | 10 | $t_1$ | $t_1$ | $t_2$ | | $t_2$ |
| . | . | . | . | . | | . |
| 64 | 64 | $t_2$ | $t_3$ | $t_4$ | | $t_1$ |
| 1 | 1 | $t_1$ | $t_2$ | $t_3$ | | $t_1$ |
| . | . | . | . | . | | . |

The counter 150 counts the clock pulses CP from the clock pulse generator 14. The ROM1 (151) is addressed by the output of the counter. As in the previous case, eight transducers operate simultaneously and are shifted one by one in response to each clock pulse. Given time control information $t_1$ to $t_4$ are read out of the memories ROM2$_1$ (401) to ROM2$_8$ (408) through the addressing by the counter 150 output. The outputs from the memories ROM2 (here corresponding to the delay control signals $D_1$ to $D_8$) are coupled with the control terminals of the switches for selecting the taps of the delay lines, thereby to select the desired delay time. With the transducers disposed with each interval 1.5 mm and each with 5 cm of focal point, if the transducers $11_1$ to $11_8$ are first driven, the taps of the delay lines to be selected are as follows. The time delay $t_1=0$ ns is selected for the delay lines $39_1$ and $39_8$, $t_2=90$ ns for the delay lines $39_2$ and $39_7$, $t_3=150$ ns for the delay lines $39_3$ and $39_6$, and $t_4=180$ ns for the delay lines $39_4$ and $39_5$. In this case, the number of the time delays, i.e. the number of the taps to be used is four (4), and if $t_1=0$, $t_2=90$ ns, $t_3=150$ ns, and $t_4=180$ ns, the outputs of the ROM2 with respect to the addresses thereof are shown in Table 2. This shows that both the electronic focusing and the linear scanning are possible. In the FIG. 5 embodiment, the variable delay lines are used commonly for the receiving and transmitting modes; however, separate delay lines may be used for the respective modes and, in this case, switches Wi1 to Wi8 and Wo1 to Wo8 are unnecessary.

While two embodiments of the invention have been illustrated and described in detail, it is particularly understood that the invention is not limited thereto or thereby.

What we claim is:

1. An ultrasonic diagnostic equipment comprising:
   a plurality of ultrasonic transducers disposed in line and divided into a plurality of groups each having a predetermined number of transducers;
   a plurality of drive pulse generators each connected directly to the corresponding one of the ultrasonic transducers, respectively, for supplying high level pulses to the respective transducers in order to transmit ultrasonic waves from the transducers;
   a plurality of gate circuits connected to the drive pulse generators, respectfully, for supplying control signals to the drive pulse generators;
   a plurality of analogue switch circuits connected to the ultrasonic transducers, respectively, for delivering signals received from the transducers in response to reflected ultrasonic waves;
   a control circuit section for producing control signals to control the gating of the gate circuits and the switching operations of the analogue switch circuits, the control circuit section including a clock pulse generator for generating clock pulse signals, a plurality of delay circuits provided corresponding to the transducers of each group through which clock pulses are supplied to the gate circuits and through which analogue signals received from the transducers are passed, a first control circuit connected to the gate circuits for controlling the gating of the gate circuits, and a second control circuit connected to the delay circuits for controlling the delay times of the delay circuits, the first control circuit generating control signals for opening the same number of gate circuits as the number of the transducers of each group with the gate circuits to be opened being shifted one by one, whereby the delayed pulse signals passed through the delay circuits and having different phases are supplied through the open gate circuits to the corresponding drive pulse generators; and
   means for processing the signals passed through the delay circuits to obtain image data corresponding to the reflected ultrasonic waves.

2. An ultrasonic diagnostic equipment according to claim 1, wherein each of said delay circuits is a variable delay line.

3. An ultrasonic diagnostic equipment according to claim 1, in which said delay means includes a plurality of delay lines provided commonly to the transducers located at the same positions of respective groups each consisting of a series of transducers.

4. An ultrasonic diagnostic equipment according to claim 3, in which said delay means is a variable delay line with taps.

5. An ultrasonic diagnostic equipment according to claim 1, in which said control circuit is a serial-parallel shift register for shifting the given stored information bit by bit in response to the clock pulse delivered from said clock pulse generator, and said shift register for generating control signals for providing a predetermined delay to each of said delay circuits, said control signals corresponding to said plurality of delay means.

6. An ultrasonic diagnostic equipment according to claim 1, in which said first and second control circuits include a counter for successively counting the clock pulse from said clock pulse generator, a first read only memory in which the control information corresponding to said transducers are stored with given addresses, a second read only memory which is provided corresponding to said delay means and the delay control information for controlling the delay time of said delay circuits in a given manner are stored with given addresses, wherein said first and second read only memories output the given control information in response to the addressing made corresponding to the contents of said counter.

* * * * *